United States Patent [19]

Shishido

[11] 4,369,767
[45] Jan. 25, 1983

[54] ENDOSCOPE SYSTEM

[75] Inventor: Yoshio Shishido, Soka, Japan

[73] Assignee: Olympus Optical Co., Ltd., Tokyo, Japan

[21] Appl. No.: 149,925

[22] Filed: May 14, 1980

[30] Foreign Application Priority Data

| May 25, 1979 | [JP] | Japan | 54-64671 |
| May 25, 1979 | [JP] | Japan | 54-64672 |
| May 25, 1979 | [JP] | Japan | 54-64674 |
| May 25, 1979 | [JP] | Japan | 54-64675 |

[51] Int. Cl.³ .......................... A61B 1/04; G03B 37/00
[52] U.S. Cl. ................................... 128/6; 354/62; 354/63; 350/502
[58] Field of Search ................ 128/4, 5, 6, 7, 8, 9; 350/19; 354/62, 63

[56] References Cited

U.S. PATENT DOCUMENTS

| 3,437,747 | 4/1969 | Sheldon | 128/6 X |
| 3,525,332 | 8/1970 | Kosaka | 128/6 |
| 3,987,463 | 10/1976 | Nishikawa et al. | 350/19 X |
| 3,994,288 | 11/1976 | Stumpf | 128/6 |
| 4,057,318 | 11/1977 | Schindl | 350/19 |
| 4,157,216 | 6/1979 | Plummer | 128/6 X |

FOREIGN PATENT DOCUMENTS 1044348  11/1958  Fed. Rep. of Germany .......... 128/4

Primary Examiner—Gene Mancene
Assistant Examiner—Robert P. Swiatek
Attorney, Agent, or Firm—Frishauf, Holtz, Goodman and Woodward

[57] ABSTRACT

An endoscope system comprises an endoscope, a camera unit, and a light source unit. A light splitting unit with a combined prism element for splitting light transmitted through an image guide is attached to an ocular section of the endoscope, and an eyepiece to which one split light travels and an additional image guide with one end face to which the other split light travels are fixed to the light splitting unit. A camera is attached to the other end of the additional image guide by means of a camera mounting unit. A light shutting plate for intercepting a light path between the prism element and the eyepiece is slidably disposed in the light splitting unit. When the light shutting plate is slid to intercept the light path, the shutter of the camera unit is released, and flash light is supplied from the light source unit to a light guide of the endoscope.

7 Claims, 12 Drawing Figures

FIG. 2
FIG. 3
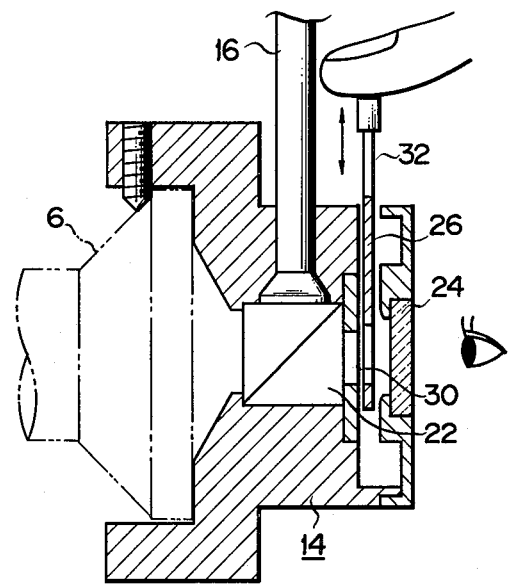
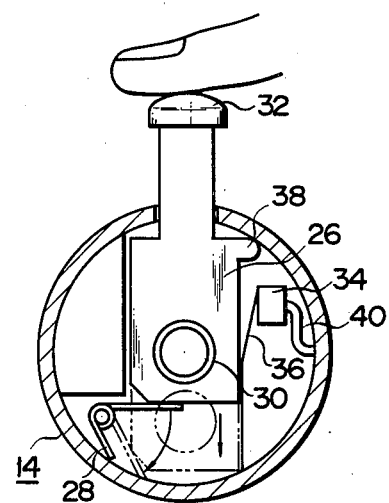
FIG. 4
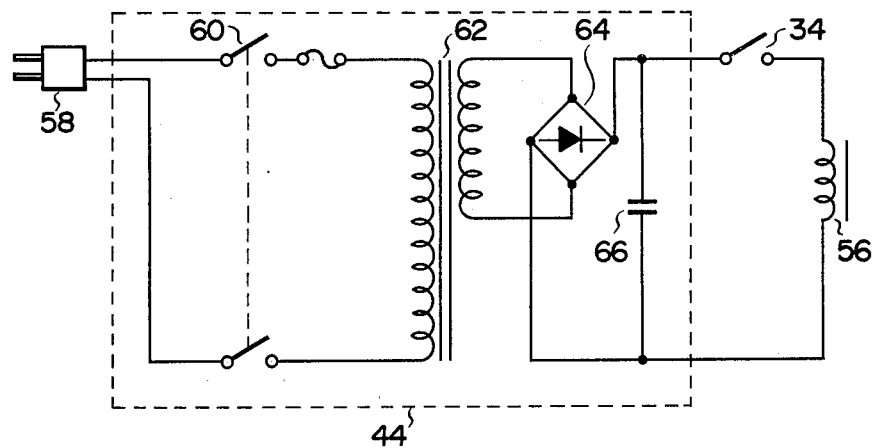

ENDOSCOPE SYSTEM

BACKGROUND OF THE INVENTION

This invention relates to an endoscope system, more specifically to a rigid endoscope system and for photographing the interior of a body cavity by means of a conventional camera unit, i.e. a single-lens reflex camera.

Generally, in a diagnosis using an endoscope, an insertion section of the endoscope is inserted into part of a human body, and a region of interest in a body cavity is observed through an ocular section of the endoscope and photographed using a camera unit. Conventionally, the camera unit is attached to the ocular section of the endoscope by means of a camera mounting unit, as stated in U.S. Pat. No. 4,182,558. Usually, an endoscope system is expected to ensure high operating efficiency, that is, to have a light and compact ocular section. If the camera unit is attached to the ocular section by means of the aforesaid camera mounting unit, however, weight is concentrated on the ocular section of the endoscope, and the ocular section increases in size, thereby deteriorating the operating efficiency of the endoscope.

Since the total weight of the system is substantial, the insertion section of a rigid endoscope, especially one with a small diameter, is liable to be bent while an operator is absorbed in his photographing operation. In inspection, moreover, the camera must be removed from the system, and the removed camera will possibly encumber the operator's action. Further, when using a camera without an automatic film advancing mechanism, the operator must perform the film advancing operation himself. Furthermore, the camera cannot be disinfected, so that it will not be able to be used when operating the endoscope under an aseptic condition, e.g. under a surgical operation.

SUMMARY OF THE INVENTION

The object of this invention is to provide a high operating-efficiency endoscope system with a compact and relatively light ocular section of an endoscope.

According to this invention, there is provided an endoscope system comprising an endoscope including an insertion section to be inserted into a body cavity and an ocular section coupled with the insertion section, a light guide and an image guide extending through the insertion section, one end of the image guide being located at the ocular section, a light source unit for supplying flash light to the light guide of the endoscope, means for splitting light transmitted through the image guide into two light paths, means for viewing a region of interest of the body cavity through the image guide and the light splitting means, the viewing means being disposed on one light path of the light splitting means, an additional image guide disposed on the other light path of the the light splitting means, whereby an image of the region of interest is transmitted through the both image guides and the light splitting means, a housing for receiving the light splitting means and holding the viewing means and the additional image guide, the housing being attached to the ocular section, light shutting means selectively operable for shutting or intercepting the light from the light splitting means toward the viewing means, located on one light path between the light splitting means and the viewing means, camera mounting means for mounting the camera unit and being provided with the additional image guide, and camera unit actuating means responsive to operation of said light shutting means for releasing the shutter of the camera unit after the light is shut off or intercepted by the light shutting means, thereby causing flash light to be supplied from the light source unit.

BRIEF DESCRIPTION OF THE DRAWINGS

FIGS. 2 and 3 are schematic longitudinal and cross sections of a light splitting unit shown in FIG. 1, respectively;

FIG. 4 shows a circuit diagram of a camera shutter actuating unit shown in FIG. 1;

DETAILED DESCRIPTION OF THE PREFERRED EMBODIMENTS

Figure 1:
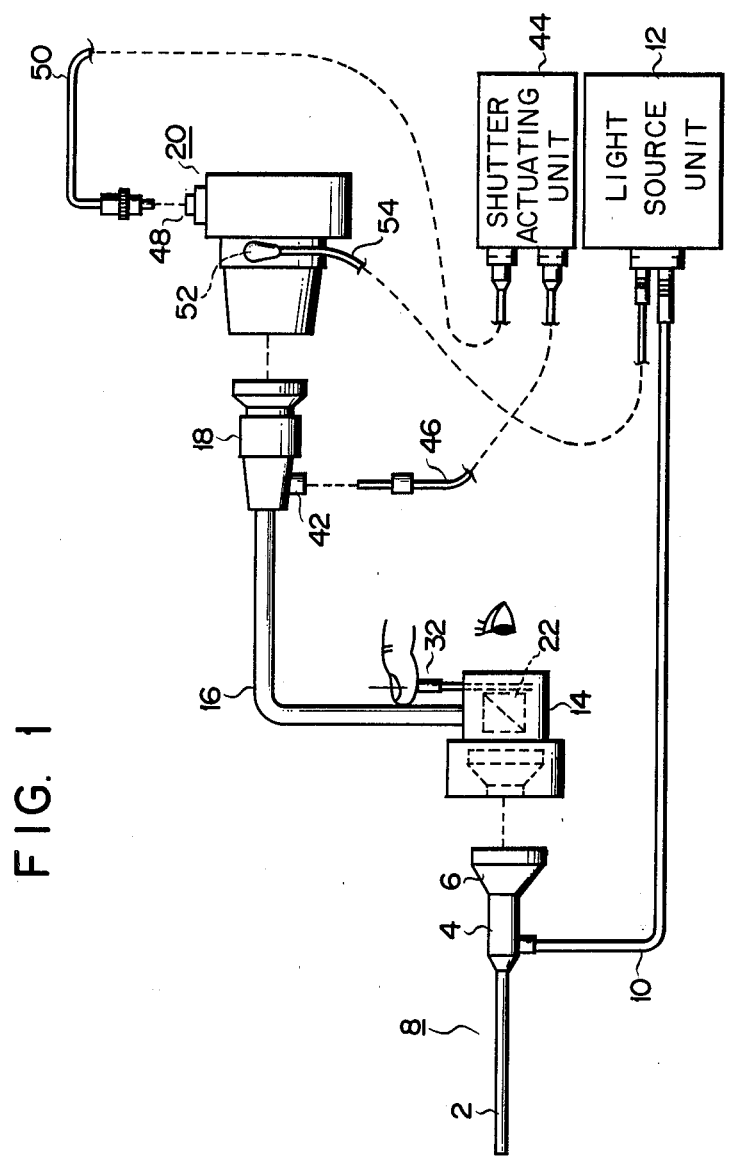
FIG. 1 is a schematic view of an endoscope system according to an embodiment of this invention.

Referring now to the drawing of FIG. 1, there is shown an endoscope system according to an embodiment of this invention. This endoscope system is provided with a rigid endoscope 8 which is composed of an insertion section 2, a handle section 4 and an ocular section 6, as illustrated. As is generally known, an image guide and a light guide extend inside the insertion section 2, one end of each guide reaching the distal end of the insertion section 2. The other end of the image guide reaches the ocular section 6, while the other end of the light guide reaches the handle section and is optically coupled with one end of a flexible light guide 10. The flexible light guide 10 extends from the handle section 4, and is coupled with a light source unit 12. In this invention, the ocular section 6 is removably fitted with a light splitting and shutting unit 14 shown in FIGS. 2 and 3. In the light splitting and shutting unit 14, there is provided a combined prism element or half mirror 22 to split incident light into two light paths. An eyepiece 24 serving as a view finder for the observation of the region of interest is disposed on one light path of the combined prism element 22, while one end or incidence face of a flexible additional image guide 16 attached to the unit 14 is located on the other light path. A camera mounting unit 18 is attached to the other end of the additional image guide 16, and a camera unit 20, e.g. a single-lens reflex camera, is mounted on the camera mounting unit 18. Interposed between the eyepiece 24 and the combined prism element 22, as shown in FIGS. 2 and 3, is a light shutting plate 26 for intercepting light directed toward the eyepiece 24. This plate 26 abuts against the housing of the unit 14, being biased by a spring member 28 and slidably disposed inside the unit 14. The plate 26 has a light transmission aperture 30 formed therein. The aperture 30 is so located as to secure the path of light from the prism 22 directed toward the eyepiece 24 while the plate 26 is being spring-biased. The light shutting plate 26 is provided with a push knob 32 extending outside the unit 14, whereby the light shutting plate 26 is caused to slide against the urging force of the spring member 28. Inside the light splitting and shutting unit 14, moreover, there is a microswitch 34 which is closed in response to the sliding action of the light shutting plate 26. Namely, a contact 36 of the microswitch 34 is located beside the plate 26, and the plate 26 has a projection 38 which engages the contact 36 to close the microswitch 34 when the plate 26 is slid downwardly. Electrical signal lines 40 electrically connected to the microswitch 34 pass through the unit 14, extend along the flexible additional image guide 16, and are connected to a connector 42 which is provided at the mounting unit 18. The connector 42 is connected with a connector cord 46 which is connected to a shutter actuating unit 44. Also, the shutter actuating unit 44 is connected with a release cord 50 which is attached to a shutter button 48 of the camera unit 20. A synchro cord 54 connected to a flash socket 52 of the camera unit 20 is connected to the light source unit 12.

Being of a well-known construction, the light source unit 12 will be excluded from the detailed description. In brief, the unit 12 comprises an electrical flash tube to emit flash light to be introduced into the light guide 10, a capacitor to supply discharge current to the flash tube, a circuit for charging the capacitor, and a triggering circuit to energize the flash tube with a synchro signal supplied from the camera unit 20 by means of the synchro cord 54. Further, the light source unit 12 includes a commutation circuit to turn off the flash tube with a light emission stop signal which is emitted from an electrically controlled exposure unit (also called an electric eye unit) incorporated in the camera unit 20 and is supplied by means of the synchro cord 54.

The shutter actuating unit 44, for example, is constructed as shown in FIG. 4. In this example, a solenoid 56 is mechanically constructed so as to press on the plunger of the release cord. That is, as shown in FIG. 4, a connector 58 to be connected to an AC power source is connected with the primary winding of a transformer 62 through a power switch 60, and a rectifier circuit 64 is connected to the secondary winding of the transformer 62. The rectifier circuit 64 is connected with a capacitor 66, which is connected in parallel with a series circuit of the solenoid 56 and microswitch 34. With such circuit, the solenoid 56 is energized by the capacitor 66 to cause the shutter button 48 to be depressed when the microswitch 34 is closed.

Constructed in the aforementioned manner, the endoscope system of this invention is operated as follows. First, the camera unit is held by an assistant operator or mounted on a tripod (not shown) or the like. A main operator operates the handle section 4 to bring the distal end of the endoscope 2 close to the desired region of interest. When it is confirmed that the desired region of interest has come in sight through the eyepiece 24, the push knob 32 is depressed, and the light shutting plate 26 is slid downwardly against the spring member 28. When the light shutting plate 26 is so operated the field of vision obtained through the eyepiece 24 is intercepted, and the microswitch 34 is closed by the projection 38. As a result, the solenoid 56 is energized to depress the shutter button 48 of the camera unit 20. As is generally known, therefore, a synchro signal is produced at the camera unit 20, the light source unit 12 is operated, and flash light is led into the light guide 10. The flash light is applied to the region of interest through the light guide inside the endoscope 2, and reflected light is projected on the light splitting and shutting unit 14 through the image guide inside the endoscope 2 and the ocular section 6. The reflected light is split into two branches of light by the light splitting and shutting unit 14. One split light is projected on the light shutting plate 26, while the other split light is introduced into the additional image guide 16 and projected on a film surface in the camera unit 20. The camera unit 20 detects the quantity of projected light, and produces a light emission stop signal when the detected quantity of light has reached a predetermined proper level, thereby stopping the light emission of the light source unit 12. In the camera unit 20, a shutter is released to be opened after the shutter button 48 is depressed, and is closed to finish a shot in a given period of time after the opening of the shutter following the stoppage of the light emission of the light source unit 12.

In the endoscope system of this invention, the camera unit is not attached to the ocular section 6 of the endoscope 8 by means of the camera mounting unit, so that no substantial weight is applied to the ocular section 6. Capable of being kept compact, moreover, the endoscope is easy to handle. Accordingly, even though the insertion section 2 of the endoscope 8 has a small diameter, it can be prevented from being broken or bent. Since the camera unit is not located in the vicinity of the ocular section 6, furthermore, photographing can be performed while disinfecting the ocular section 6 and other sections. Also, the shutter of the camera unit 20 may practically be released at the unit 14 which is attached to the ocular section 6, so that the main operator can take a photograph the moment he finds the region of interest by operating the endoscope 8, thus enjoying an efficient diagnosis. Further, since the field of vision obtained through the eyepiece 24 is intercepted at photographing, the main operator's eye may be protected from flash light.

Referring now to FIGS. 5 to 11, there will be described another embodiment of the endoscope system of this invention. In these drawings, like reference numerals refer to the same parts of FIGS. 1 to 4, and description of such parts is omitted.

Figure 5:
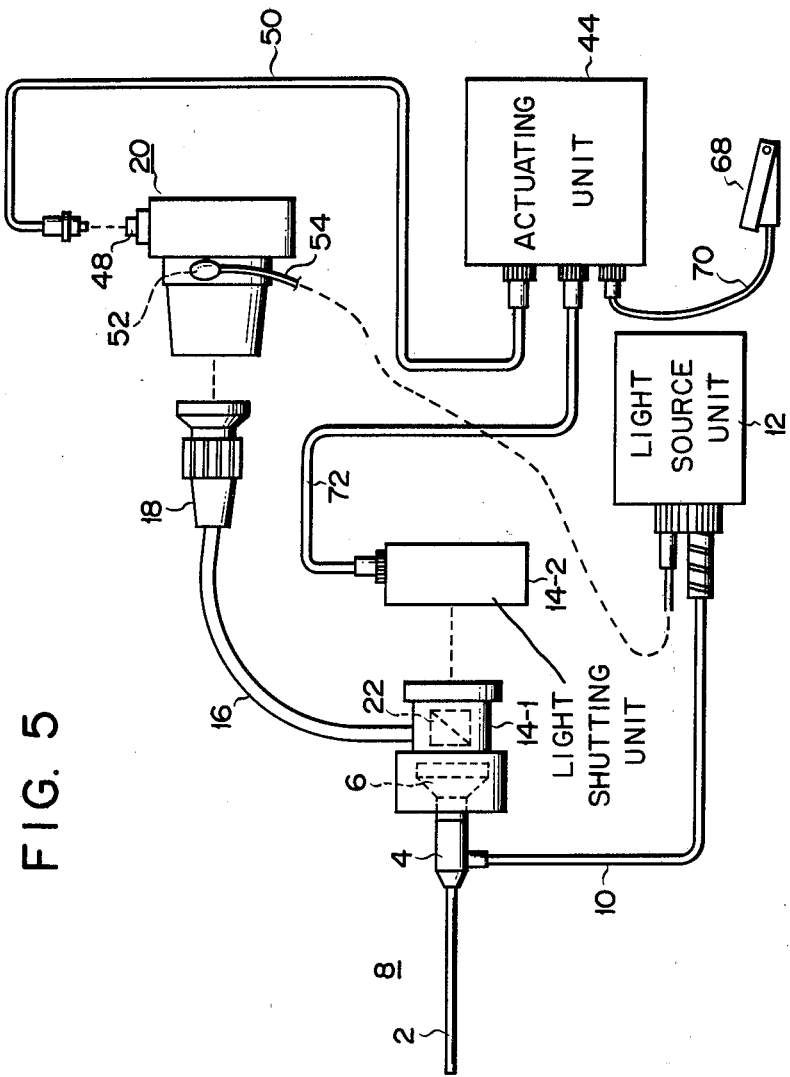
FIG. 5 is a schematic view of an endoscope system according to another embodiment of the invention.
Figure 6:
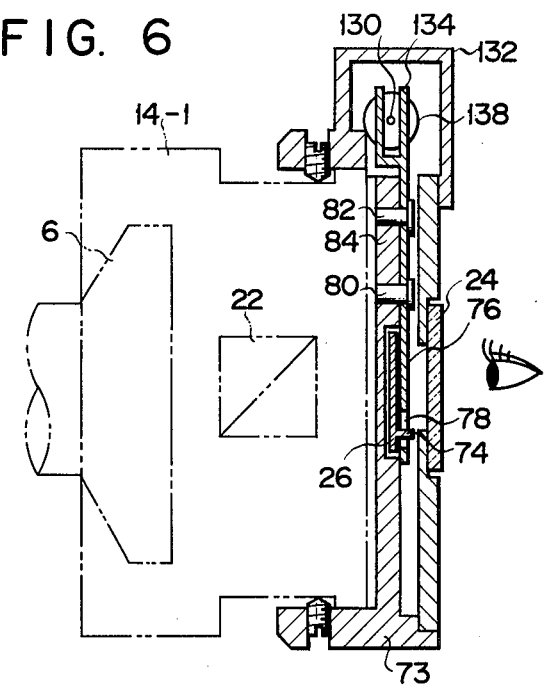
FIGS. 6 and 7 are schematic longitudinal and cross sections of a light splitting unit shown in FIG. 5, respectively.
Figure 7:
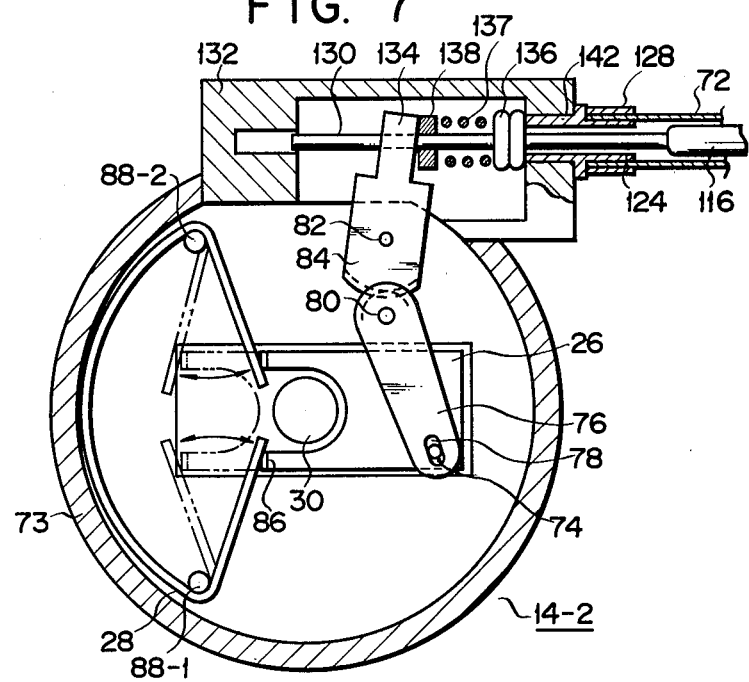

The endoscope system shown in FIG. 5 is of basically the same construction as the system shown in FIG. 1 except the following. A light splitting and shutting unit 14 is not provided with a push knob 32 for releasing the shutter of a camera unit 20, but with a footswitch 68 connected with a light shutting plate and shutter actuating unit 44 by means of an electric signal cord 70. The light splitting and shutting unit 14 is separated into two subunits; a light splitting unit 14-1 removably attached to an ocular section 6 and a light shutting unit 14-2 removably attached to the unit 14-1. The light shutting unit 14-2 is mechanically coupled to the unit 44 by means of a light shutting plate actuating cord 72. As shown in FIGS. 6 and 7, a light shutting plate 26 is slidably disposed inside a housing 73 of the light shutting unit 14-2 so as to be slideable over a light transmission aperture 30 to selectively cover aperture 30. A pin 74 protruding from one end portion of the light shutting plate 26 is fitted in a slot 78 formed through one end portion of a lever 76. The other end portion of the lever 76 is swingably mounted on a pin 80, and is engagedly connected with one end portion of a lever 84 which is swingably mounted on a pin 82 at its middle portion.

As shown in FIG. 7, moreover, the light shutting plate 26 is provided with a spring holder 86 with two projected ends on which both ends of a spring 28 abut, respectively. The spring 28 is held between pins 88-1 and 88-2 and the inner periphery of the housing 73 of the unit 14-2, thereby urging the light shutting plate 26. While the light shutting plate 26 is being urged by the spring 28, the aperture 30 is not closed, and a light path for observation is maintained between the prism element 22 and the eyepiece 24.

Figure 8:
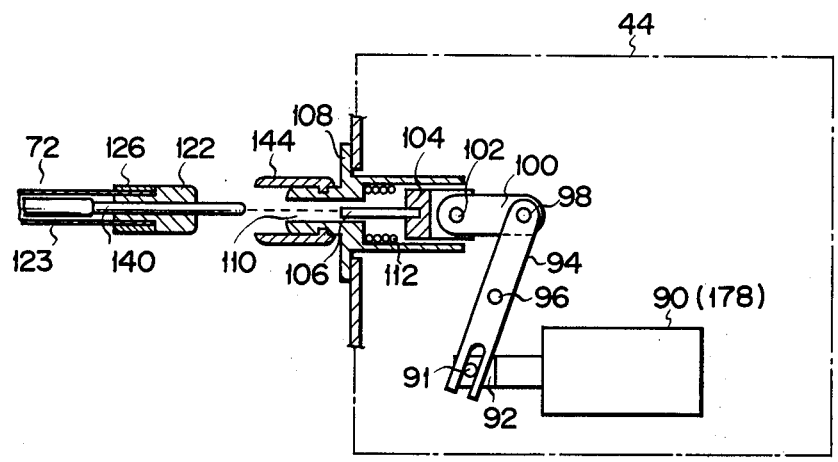
FIG. 8 is a partial sectional view schematically showing a mechanical power generating mechanism built in a camera shutter and light shutting plate actuating unit shown in FIG. 5.

Inside the actuating unit 44, there are disposed a pair of solenoids 90, 178 which actuate the light shutting plate and release the shutter in conjunction with the mechanism of the light shutting unit 14-2. FIG. 8 shows only one solenoid 90 for simplicity. A core 92 of the solenoid 90 is connected with one end portion of a lever 94 by means of a pin 91. The lever 94 is swingably mounted on a pin 96 at its middle portion, having the other end portion connected with a lever 100 by means of a pin 98. The other end portion of the lever 100 is connected with a piston 104 by means of a pin 102, and a bar 106 extends from the front portion of the piston 104. The piston 104 is slidably disposed inside a connector 108 of the cord 72, the connector 108 having a guide path 110 through which the bar 106 is passed. The piston 104 is biased by a spring 112 set in the connector 108.

Figure 9:
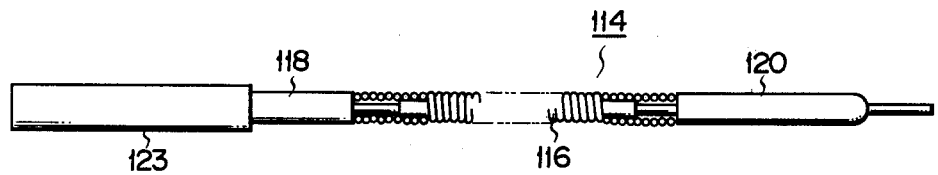
FIG. 9 is a partial sectional view showing a mechanical power transmission member contained in a light shutting plate actuating cord shown in FIG. 5.

A mechanical power transmission member 114 is inserted in the actuating cord 72 for transmitting mechanical power to the light shutting plate 26. As shown in FIG. 9, the mechanical power transmission member 114 is composed of a tight coil 116 capable of freely bending to secure transmission of strokes in the direction of compression, and rigid shafts 118 and 120 fixed respectively to both end portions of the coil 116 by soldering, etc. The mechanical power transmission member 114 is inserted in and covered with a pipe 123 made of flexible plastic material which cannot be distorted by heat or chemicals and can be curved with the curvature of the mechanical power transmission member 114. Further, connectors 122 and 124 are fixed to both end portions of the pipe 123 by means of outer pipes 126 and 128, respectively.

As shown in FIG. 7, a transmission shaft 130 at one end portion of the mechanical power transmission member 114 is inserted in a bore of a case 132 attached to the housing 73 of the light shutting unit 14-2 as well as between bifurcate legs 134 of the lever 84. Further, a nut 136 and a slidable washer 138 are mounted on the shaft 130, and a spring 137 is interposed between the nut 136 and washer 138. The legs 134 of the lever 84 are so disposed as to abut against the washer 138 to be rocked thereby.

As shown in FIG. 8, moreover, the other end portion of the mechanical power transmission member 114, i.e. a shaft 140, is fitted in and connected with a guide path 110 of a connector 108. The connectors 122 and 124 at both end portions of the pipe 123 are fixedly connected with a fitting hole 142 of the case 132 and a coupling pipe 144 of the connector 108, respectively.

Figure 10:
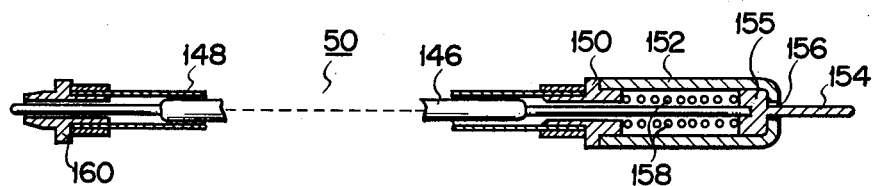
FIG. 10 is a sectional view of a shutter release cord shown in FIG. 5.

Referring now to FIG. 10, the release cord 50 will be described in detail. The release cord 50 has one end coupled to a mechanism including the solenoid 178 as shown in FIG. 8, and the other end coupled to the shutter button of the camera unit 20. The release cord 50 includes a flexible pipe 148 through which a mechanical power transmission member 146 extends, and a connector 150 is attached to one end of the pipe 148. The connector 150 is fixedly connected with a cylinder 152 in which a slideable member 155 with a pin 154 protruding therefrom is slidably contained. The member 155 is fixedly connected with one end portion of the mechanical power transmission member 146, and the pin 154 is projected out of a through hole 156 of the cylinder 152. Interposed between the member 155 and the connector is a spring 158 whereby the member 155 is urged to return the mechanical power transmission member 146. Further, a connector 160 is attached to the other end portion of the pipe 148, and can be removably coupled with the shutter button 48 of the camera unit 20. Also, in the same manner as shown in FIG. 8, the pin 154 is inserted in the guide path 110, and the cylinder 152 is removably connected to the coupling pipe 144.

Figure 11:
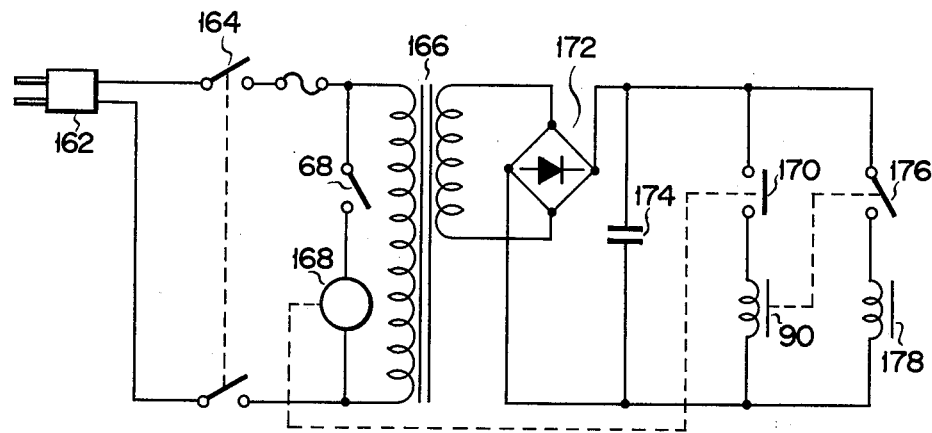
FIG. 11 is a diagram showing a circuit diagram in the camera shutter and light shutting plate actuating unit shown in FIG. 5.

The light shutting plate and shutter actuating unit 44 includes a circuit as shown in FIG. 11. In this circuit, the primary winding of a transformer 166 is connected through a power switch 164 to a connector 162 which is connected to an AC power source. Further, the primary winding of the transformer 166 is connected with a series circuit of the footswitch 68 and a timer 168 with a contact 170, while the secondary winding of the transformer 166 is connected with a capacitor 174 through a rectifier circuit 172. The capacitor 174 is connected in parallel with a series circuit of the timer contact 170 and the first solenoid 90 for actuating the light shutting plate 26, and is also connected in parallel with a series circuit of a switch 176 which closes when the attracting operation of the first solenoid 90 is finished and a second solenoid 178 for releasing the shutter. With this circuit, the second solenoid 178 is operated with a time delay after the operation of the first solenoid 90. Namely, when the footswitch 68 is closed, the timer 168 is actuated to close its contact for a given period of time. During such period, the first solenoid 90 is energized by the capacitor 174. When the first solenoid 90 is energized and the core 92 of the solenoid 90 is attracted to the very limit, the switch 176 is closed, and the second solenoid 178 is energized with a time delay. Such time delay is provided for the operations of the first and second solenoids 90 and 178 in order that the light source unit 12 may be prevented from being operated to project flash light on a viewer's eye after the light shutting plate 26 is entirely slid to close the light transmitting hole 30.

The endoscope system according to aforementioned alternative embodiment of the invention is operated in the following manner. First, the insertion section 2 of the endoscope is inserted into a body cavity for observation. Thereafter, the footswitch 68 is depressed to photograph a desired region of interest. By this, the core 92 of the solenoid 90 for actuating the light shutting plate 26 is attracted to rock the lever 94 counterclockwise around the pin 91. As a result, the piston 104 is advanced by means of the lever 100 against the biasing force of the spring 112. The advance of the piston 104 causes the shaft 140 to be pushed by the pin 106 to advance the mechanical power transmission member 114, and thus the lever 134 in the case 132 is rocked counterclockwise by the washer 138, as shown in FIG. 7. The rocking of the lever 134 causes the lever 76 to rock clockwise to slide the light shutting plate 26 against the biasing force of the spring 28, thereby closing the light transmitting hole 30.

After the light transmitting hole 30 is closed, the solenoid 178 for actuating the shutter button 48 is energized to advance the pin 106 of the piston 104 in the same manner as aforesaid. Thus, the pin 154 and the member 155 inside the cylinder 152 are advanced against the biasing force of the spring 158, so that the mechanical power transmission member 146 is advanced. As a result, the shutter 48 of the camera unit 20 is operated by the shaft of the mechanical power transmission member 146. Thus, the light source unit 12 is operated to produce flash light, and a photographing operation is completed.

When the footswitch 68 is released or when the operating time of the timer 168 is terminated, the light shutting plate 26 is returned by the biasing force of the spring 28 to open the light transmitting hole 30, and the lever 76 is rocked counterclockwise to return the mechanical power transmission member 114 in the cord 72. At the same time, the mechanical power transmission member 146 in the cord 50 is returned to its initial position by the biasing force of the spring 158.

Since the effective operating stroke of the mechanical power transmission member 114 may vary with the curvature of the cord 72, an increment of the stroke can be absorbed by reducing the operating stroke of the lever 84 and shifting the lock nut 136 to reduce the dimension of the spring 137 in the direction of compression.

Also, the stroke of the light shutting plate 26 can be determined properly by reducing the radius of the rocking circle of the lever 76 and extending the arm.

Figure 12:
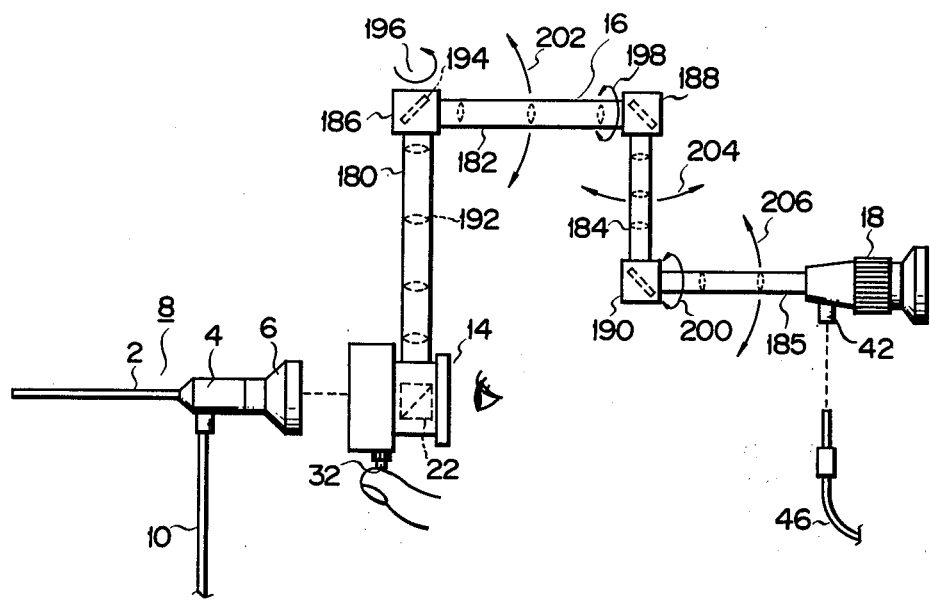
FIG. 12 schematically shows a modification of the endoscope system of the invention.

Although the additional image guide 16 in the above-mentioned embodiments is flexible, it may alternatively be rigid. That is, a plurality of rigid coupling pipes 180, 182, 184 and 185 may be coupled with one another by means of joint sections 186, 188 and 190, as shown in FIG. 12. A plurality of lens elements 192 are arranged on each of the coupling pipes 180, 182, 184 and 185 so as to be able to transmit a light split by the prism element 22, that is, an image of the region of interest. The joint sections 186, 188 and 190 each contain a reflector 194 which is so disposed as to reflect light introduced from one of each adjacent pair of coupling pipes coupled by means of the joint section concerned on the other coupling pipe. Moreover, these coupling pipes 180, 182, 184 and 185 are attached severally to the joint sections 186, 188 and 190 so as to be able to rotate in the direction of arrows 196, 198 and 200, and also to swing in the vertical or horizontal directions around the respective centers of the reflectors 194 in the joint sections, as indicated by arrows 202, 204 and 206.

As described above, even though the additional image guide 16 is rigid, the endoscope may be handled with ease as long as it is movable and swingable. In particular, the operating efficiency of the endoscope may be improved by suspending the additional image guide 16 so as to minimize the weight of the guide 16 applied to the ocular section 6.

Thus, according to this invention, there may be provided a high operating-efficiency endoscope system with a compact and relatively light ocular section of an endoscope.

What is claimed is:

1. An endoscope system for use with a camera unit, comprising:

an endoscope including an insertion section to be inserted into a body cavity, an ocular section coupled with said insertion section, and a light guide and a first image guide extending through said insertion section, one end of said first image guide being located at said ocular section;

a light source unit for supplying flash light to said light guide of said endoscope;

means for splitting light transmitted through said first image guide into two light paths;

viewing means for viewing a region of interest of the body cavity through said first image guide and said light splitting means, said viewing means being disposed on one light path of said light splitting means;

an additional image guide disposed on the other light path of said light splitting means, whereby an image of the region of interest is transmitted through said first and additional image guides and said light splitting means;

a housing for receiving said light splitting means and holding said viewing means and said additional image guide, said housing being attached to said ocular section;

light shutting means which is selectively operable for shutting or intercepting the light from said light splitting means toward said viewing means, said light shutting means being located in said one light path between said light splitting means and said viewing means;

camera mounting means for mounting said camera unit, said camera mounting means being coupled with said additional image guide; and camera unit actuating means responsive to operation of said light shutting means to a light intercepting position for releasing the shutter of said camera unit after the light is shut off or intercepted by said light shutting means, and for thereby causing flash light to be supplied from said light source unit.

2. An endoscope system according to claim 1, wherein said light shutting means is slidably disposed in said housing and comprising a spring member disposed in said housing for biasing said light shutting means in a light passing position, said light shutting means having a light transmission region which is located on said one light path to pass light on said one light path while said light shutting means is spring-biased at said light passing position.

3. An endoscope system according to claim 2 further comprising an electrical switch means disposed in said housing and operatively coupled to said light shutting means so as to be closed by said light shutting means when said light shutting means is slid from its light passing position to a light intercepting position, said switch means being coupled to said camera unit actuating means for energizing same to cause said shutter release and flash light to be supplied from said light source unit.

4. An endoscope system according to claim 3 further comprising a connecting line for electrical signal transmission connected between said electrical switch means and said camera unit actuating means for shutter release and flash light supply, said connecting line comprising a connector coupled to said camera mounting means, a first electrical line connected between said connector and said switch means and extending along said additional image guide, and a second electrical line connected between said camera unit actuating means and said connector.

5. An endoscope system according to claim 2, wherein said camera unit actuating means includes means for sliding said light shutting means, and mechanical coupling and transmission means coupling said camera unit actuating means to said means for sliding said light shutting means; said endoscope system further comprising switch means for energizing said camera unit actuating means.

6. An endoscope system according to claim 1, wherein said additional image guide is flexible.

7. An endoscope system according to claim 1, wherein said additional image guide is rigid.

* * * * *